(12) United States Patent
Bernardoni

(10) Patent No.: US 7,931,571 B2
(45) Date of Patent: Apr. 26, 2011

(54) HIP FLEXION ASSIST ORTHOSIS OR HIP KNEE EXTENSION ASSIST ORTHOSIS

(76) Inventor: Gene Paul Bernardoni, Chicago, IL (US)

( * ) Notice: Subject to any disclaimer, the term of this patent is extended or adjusted under 35 U.S.C. 154(b) by 848 days.

(21) Appl. No.: 11/605,042

(22) Filed: Nov. 28, 2006

(65) Prior Publication Data
US 2008/0125685 A1   May 29, 2008

(51) Int. Cl.
A63B 21/02 (2006.01)
A63B 71/00 (2006.01)
G09B 19/00 (2006.01)
A61H 1/00 (2006.01)
A61F 5/00 (2006.01)

(52) U.S. Cl. .......... 482/124; 482/74; 482/121; 434/255; 601/23; 602/26; 602/23

(58) Field of Classification Search .............. 482/74, 482/121, 124, 907; 602/18, 19, 23, 25–26; 434/247, 255; 601/23
See application file for complete search history.

(56) References Cited

U.S. PATENT DOCUMENTS

| | | | |
|---|---|---|---|
| 1,548,711 A | 8/1925 | Cooper | |
| 1,562,294 A | 11/1925 | Cooper | |
| 1,608,032 A | 11/1926 | McNabb | |
| 4,252,112 A | 2/1981 | Joyce | |
| 4,602,627 A | 7/1986 | Vito et al. | |
| 4,913,136 A | 4/1990 | Chong et al. | |
| 5,172,703 A | 12/1992 | Tiede et al. | |
| 5,203,754 A * | 4/1993 | Maclean | 482/124 |
| 5,308,305 A * | 5/1994 | Romney | 482/124 |
| 5,330,417 A * | 7/1994 | Petersen et al. | 602/16 |
| 5,336,151 A * | 8/1994 | Van Ballegooie | 482/124 |
| 5,465,428 A * | 11/1995 | Earl | 2/238 |
| 5,647,827 A * | 7/1997 | Gutkowski et al. | 482/124 |
| 5,743,837 A * | 4/1998 | Dias et al. | 482/124 |
| 5,792,034 A * | 8/1998 | Kozlovsky | 482/124 |
| 5,813,954 A * | 9/1998 | Wilkinson | 482/124 |
| 5,820,534 A * | 10/1998 | Vadher | 482/124 |
| 5,860,944 A * | 1/1999 | Hoffman, Jr. | 602/19 |
| 5,895,366 A | 4/1999 | Bzoch | |
| 5,993,362 A * | 11/1999 | Ghobadi | 482/124 |
| 6,099,446 A * | 8/2000 | Johnson et al. | 482/124 |
| 6,129,691 A | 10/2000 | Ruppert | |
| 6,190,342 B1 | 2/2001 | Taylor | |
| 6,213,922 B1 * | 4/2001 | Afanasenko et al. | 482/124 |
| 6,368,256 B1 * | 4/2002 | Rumbaugh | 482/121 |
| 6,428,495 B1 * | 8/2002 | Lynott | 602/23 |
| 6,436,065 B1 * | 8/2002 | Mitchell | 602/19 |
| 6,837,834 B2 * | 1/2005 | Basting | 482/124 |
| 7,175,604 B2 | 2/2007 | Cole | 602/28 |
| 7,314,437 B2 * | 1/2008 | Frappier | 482/124 |
| 7,549,970 B2 * | 6/2009 | Tweardy | 602/18 |
| 2002/0068667 A1* | 6/2002 | Strachan | 482/124 |
| 2003/0092545 A1* | 5/2003 | Koscielny et al. | 482/124 |
| 2003/0130098 A1* | 7/2003 | Marco | 482/124 |
| 2003/0195092 A1* | 10/2003 | Basting | 482/124 |

(Continued)

Primary Examiner — Loan Thanh
Assistant Examiner — Sundhara M Ganesan

(57) ABSTRACT

An apparatus suitable for imitating one or more muscle members of a human user during physical therapy, wherein the apparatus is configured to be used in conjunction with the human user having a waist and a leg having a knee. The apparatus includes an adjustable waist belt configured to be secured around the human user's waist and a lower leg support configured to encircle the human user's leg in a vicinity of the knee. The apparatus further includes an elastic member configured to provide an adjustable tensile resistance between the waist belt and the lower leg support.

19 Claims, 3 Drawing Sheets

U.S. PATENT DOCUMENTS

| | | | |
|---|---|---|---|
| 2003/0208147 A1* | 11/2003 | Reinecke et al. | 602/19 |
| 2004/0152569 A1* | 8/2004 | Lerner | 482/124 |
| 2004/0230150 A1* | 11/2004 | West | 602/19 |
| 2005/0015035 A1* | 1/2005 | Sansone et al. | 602/19 |
| 2005/0054960 A1* | 3/2005 | Telles et al. | 602/19 |
| 2005/0282689 A1* | 12/2005 | Weinstein | 482/124 |
| 2006/0040807 A1* | 2/2006 | Miller | 482/124 |
| 2006/0063651 A1* | 3/2006 | Sload | 482/124 |
| 2006/0105892 A1* | 5/2006 | Wilson | 482/121 |
| 2006/0229175 A1* | 10/2006 | Frappier | 482/124 |
| 2006/0264791 A1* | 11/2006 | Frank | 602/19 |
| 2006/0264971 A1* | 11/2006 | Akahoshi | 606/107 |
| 2007/0004570 A1* | 1/2007 | Afanasenko et al. | 482/124 |
| 2007/0004571 A1* | 1/2007 | Gonzalez | 482/124 |
| 2007/0066460 A1* | 3/2007 | Torres | 482/124 |
| 2007/0135279 A1* | 6/2007 | Purdy et al. | 482/124 |
| 2007/0213186 A1* | 9/2007 | Longo | 482/121 |
| 2007/0287616 A1* | 12/2007 | Weaver | 482/124 |
| 2008/0194390 A1* | 8/2008 | Todd | 482/124 |

* cited by examiner

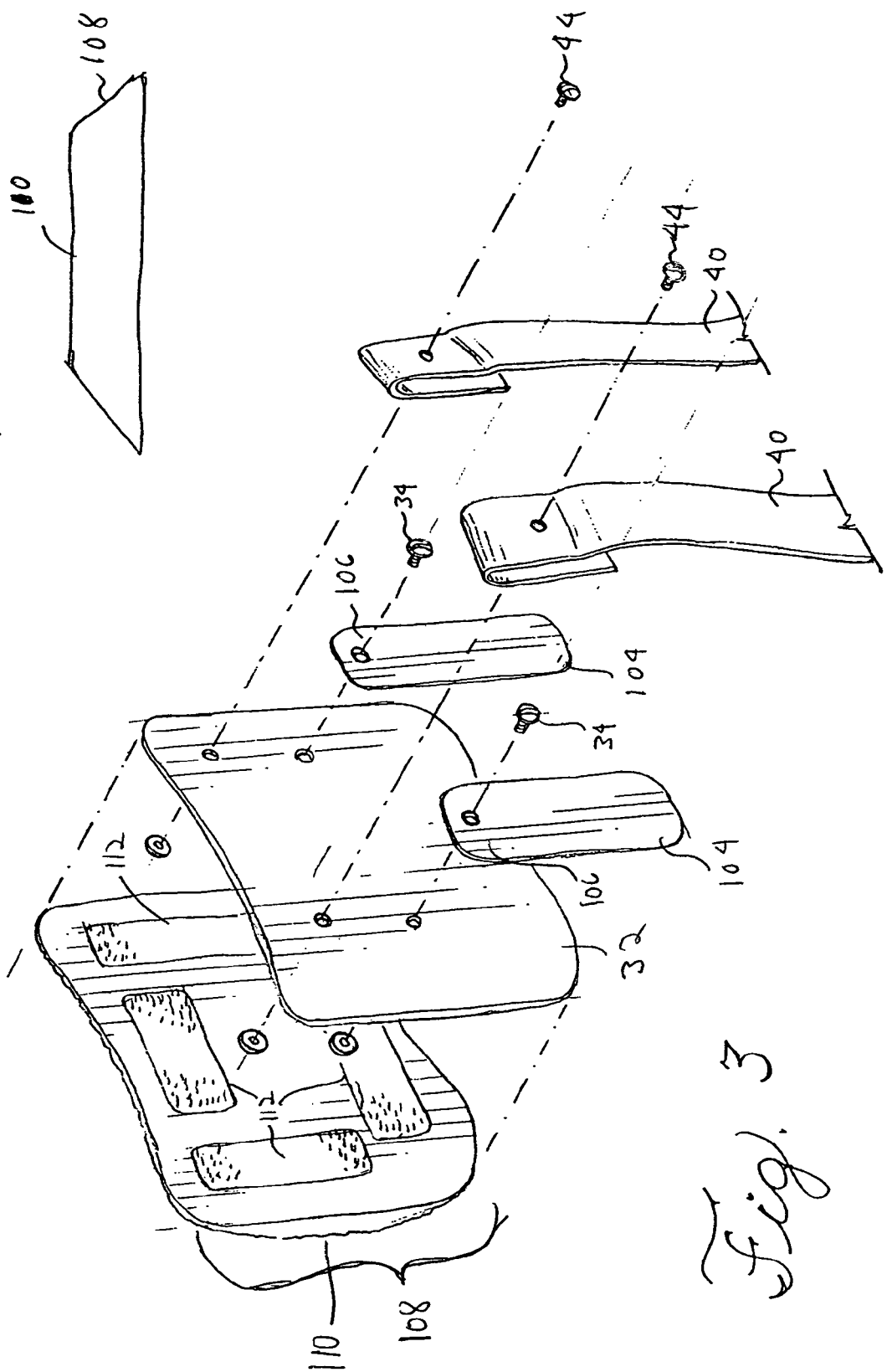

HIP FLEXION ASSIST ORTHOSIS OR HIP KNEE EXTENSION ASSIST ORTHOSIS

BACKGROUND OF THE INVENTION

1. Field of the Invention

The present invention relates to devices and methods for improving muscle and joint function, aiding weak muscles and/or slowing muscle deterioration for people who are living with muscle weakening conditions, such as muscular dystrophy, stroke and polio. The present invention allows such people to continue to ambulate longer and ambulate with more stability and safety than they could without using the present invention.

2. Discussion of Related Art

Muscular dystrophy is a genetic disorder that gradually weakens the body's muscles. In particular, incorrect or missing genetic information prevents the body from making the distrophin proteins it needs to build and maintain healthy muscles. While the genetic defect is present at birth, the weakness in the muscles most often only becomes evident in early childhood when the child begins to walk. There are other forms of muscular dystrophy wherein other symptoms don't appear until later in childhood.

In the case of a child who is diagnosed with muscular dystrophy, that child gradually loses the ability to do basic activities, such as walking, sitting upright, breathing easily, and moving the arms and hands. In the basic activities that depend on postural muscles, such as those of the pelvic girdle and the quadricep muscles are weakened to an extent that ambulation is affected early. In the different types of muscular dystrophy, the severity of the effect on the muscles results in different degrees of muscle weakness. In the case of Duchenne muscular dystrophy, the pelvic muscles begin to weaken around age 2 followed by the muscles of the upper leg (quads) that assist in ambulation and later the muscles weaken in the shoulders and the arms. Becker muscular dystrophy is similar to Duchenne muscular dystrophy in the pattern of how it affects the muscles, but begins in a person's teen years and progresses more slowly. Limb-girdle muscular dystrophy typically begins to reveal itself when kids are between 8 and 15 years old. This form of muscular dystrophy progresses slowly, affecting the pelvic and shoulder girdles, upper legs (quads), ankles, dorsiflexors, planarflexors and back muscles. In the case of Facioscapulohumeral muscular dystrophy, the upper arm, shoulders and upper back lose strength first followed by the legs and pelvic muscles of the person.

In response to the symptoms of losing muscle strength, doctors are working to improve muscle and joint function for people living with the condition. One avenue in improving muscle and joint function has been to perform physical therapy on the muscle groups, such as the pelvic muscles and joints, that are most affected by the condition so as to maintain range of motion at the joints. Such physical therapy allows weaker muscles to continue to function and prolong the ability to stand and ambulate.

One disadvantage with physical therapy is that it only occurs at intermittent times of the day and week.

A second disadvantage with physical therapy is that muscular dystrophy is a progressive disease without any hope of strengthening the afflicted muscles. The only hope is to maintain range of motion at the joints and prevent contractures This is best achieved by facilitating ambulation and standing.

SUMMARY OF THE INVENTION

One aspect of the present invention regards a muscle imitation apparatus that includes a waist belt configured to be secured around a user's waist and an elastic member having a first end and a second end, wherein the first end is coupled to the waist belt. A lower leg support is coupled to the second end of the elastic member, wherein the lower leg support is configured to encircle the user's leg in a vicinity of a patellar tendon of the user, such that the elastic member creates an adjustable tensile resistance when the user moves the leg and the lower leg support is only coupled to the elastic member when the rehabilitation apparatus is worn by the user.

A second aspect of the present invention regards a method suitable for imitating one or more muscle members of a patient during physical therapy. The method includes identifying a compromised body member of a user that requires physical therapy and placing an adjustable waist belt around the user's waist. The method further includes placing a lower leg support in a position that encircles the user's leg in a vicinity of a patellar tendon of the leg and adjusting an elastic member coupled between the adjustable waist belt and the lower leg support to provide an adjustable tensile force for purposes of imitating one or muscles of the compromised body member.

A third aspect of the present invention regards an apparatus suitable for imitating one or more muscle members of a user during physical therapy that includes an adjustable waist belt configured to be secured around a user's waist and an elastic member having a first end and a second end. The apparatus further includes means for coupling the first end of the elastic member to the waist belt, means for securing the second end of the elastic member to the user's knee and means for tensioning the elastic member between the waist belt and the means for securing.

A fourth aspect of the present invention regards an apparatus suitable for imitating one or more muscle members of a human user during physical therapy, wherein the apparatus is configured to be used in conjunction with the human user having a waist and a leg having a knee. The apparatus includes an adjustable waist belt configured to be secured around the human user's waist and a lower leg support configured to encircle the human user's leg in a vicinity of the knee. The apparatus further includes an elastic member configured to provide an adjustable tensile resistance between the waist belt and the lower leg support.

A fifth aspect of the present invention regards a muscle imitation apparatus that includes a waist belt configured to be secured around a user's waist and a back support attached to the waist belt. The apparatus further includes an elastic member having a first end and a second end, wherein the first end is coupled to the back support and the second end is coupled to a lower leg system.

A sixth aspect of the present invention regards a method suitable for imitating one or more muscle members of a patient during physical therapy, the method including identifying a compromised body member of a user that requires physical therapy and placing an adjustable waist belt around the user's waist. The method further includes placing a lower leg support in a position that encircles the user's leg in a vicinity of a patellar tendon of the leg and coupling an elastic member between the adjustable waist belt and the lower leg support to provide an adjustable tensile force for purposes of imitating one or muscles of the compromised body member. The method further includes placing a pivoting back support against a back of the user, wherein the back support is coupled to the elastic member.

Each of the above aspects of the present invention provides the advantage that it allows that physical therapy be performed on muscles on a more continuous manner throughout the day and the week.

Further characteristics and advantages of the present invention will become apparent in the course of the following description of an exemplary embodiment by the drawings.

BRIEF DESCRIPTION OF THE DRAWINGS

FIG. 3 is an exploded, rear, perspective view of an embodiment of a back support to be used with the muscle imitation apparatus of FIG. 2; and FIG. 4 is a cross-sectional view of a pad to be used with the muscle imitation apparatus of FIGS. 2 and 3.

DETAILED DESCRIPTION OF THE PREFERRED EMBODIMENTS

Figure 1:
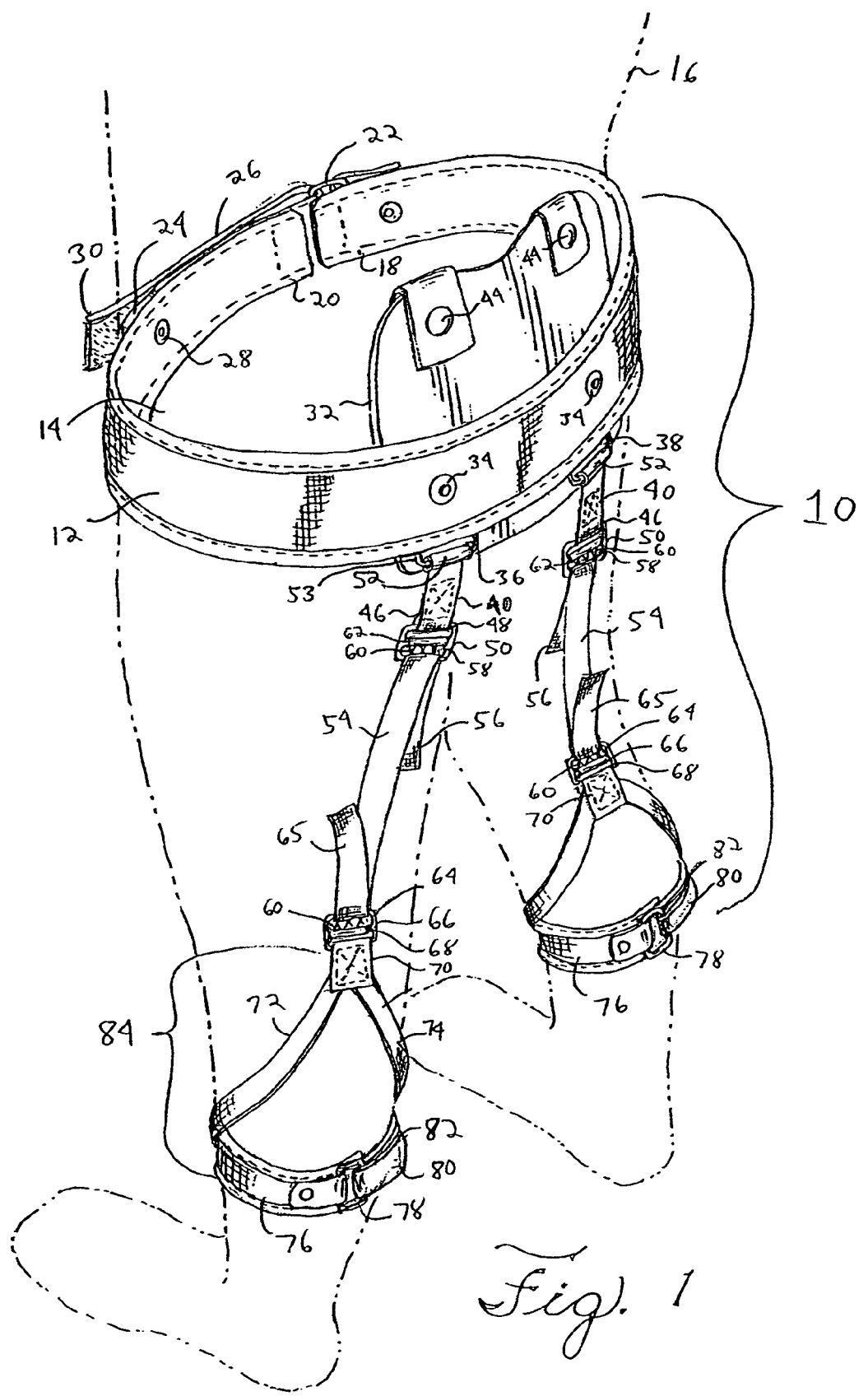
FIG. 1 is a rear, perspective view of an embodiment of a muscle imitation apparatus in accordance with the present invention.

Referring now to FIG. 1, a muscle imitation or ambulation apparatus, such as hip knee extension assist orthosis 10, includes a waist belt 12 that is configured to be adjusted in size so as to be secured around a waist 14 of a user 16. The waist belt 12 is made of a durable material, such as leather or the material know under the trademark Dacron. The waist belt 12 has a width and length that can be varied depending on the size of the waist 14 of the user 16. The waist belt 12 is a strap that has two free ends 18, 20. Attachment of the free ends 18, 20 to one another can be accomplished in a variety of ways. For example, one end 18 has a metal loop 22 attached thereto. The other end 20 has one end 24 of a hook and loop strap 26, such as that sold under the trademark Velcro, attached thereto via a rivet 28. As shown in FIG. 1, the other end 30 of the strap 26 is passed through the loop 22 and double backed so as to have the end 30 attached to a portion of the hook and loop strap 26 attached to waist belt 12.

Another embodiment for attaching the waist belt 12 is to use a well-known buckle having a metal loop and a pivotable male member attached to the free end 20. The other end 18 of the waist belt 12 has one or more holes or openings. The end 18 is passed through the metal loop and the male member is passed through one of the holes so as to provide a snug fit about the waist 14.

A back support 32 is attached to a rear portion of the waist belt 12 via a pair of rivets 34 or other appropriate attachment devices. The back support 32 extends above the top edge of the waist belt 12 so as to rotate forward against the lower lumbar area of the body when tensile forces develop in elastic straps 54. The back support 32 extends above the waist belt 12 by an amount that is greater than the amount the lower portion of the back support 32 extends below the waist belt 12. Thus, the back support 32 is asymmetrically positioned with respect to a line that is positioned approximately midway on the waist belt 12 and extends along the length of the waist belt 12. The back support 32 is made of a durable plastic material, such as polypropylene or colene. As viewed from the front of the user, the back support 32 has a generally flat portion where it overlaps the waist belt 12 and then is concave-like for those portions positioned above the waist belt 12. The shape is chosen so as to conform somewhat to the lordosis of the lower lumbar spine.

As shown in FIG. 1, a lower portion of the back support 32 has a pair of slots 36, 38 that are positioned below the bottom edge of the waist belt 12 and attached to waist belt 12 via rivets 34. Regarding slot 36, a strap 40 has one end (not shown) that is passed through slot 36 and attached to the back support 32 via a rivet 44. The other end 46 of the strap 40 is passed through a slot 48 of an attachment mechanism, such as buckle 50, and reattached to the strap 40 by stitching or other appropriate attachment devices. Many types of buckles can be used for buckle 50. For example, the buckle 50 may have a rotating axle with one or more male members extending therefrom.

Note that a plastic roller/cylinder 52 surrounds a bottom portion of a metal loop 53 (partially shown) that is attached to a metal flange (not shown). The metal flange is attached to the back support 32 and waist belt 12 via rivet 34. As shown in FIG. 1, the strap 40 is trapped between the cylinder 52 and the portion of the back support 32 below the slot 36. The cylinder 52 allows for the strap 40 to pivot more easily as the corresponding elastic strap 54 is tensioned and reduces abrasion to the end 46 of strap 40.

A similar strap 40 is inserted through the slot 38 and attached to the back support 32. The strap 40 is trapped by a cylinder 52 as well. A buckle 50 is attached to the free end 46 of the strap 40 in the same manner as described previously with respect to the other strap 40.

An elastic member 54 is coupled to the waist belt 12 via an attachment mechanism, such as buckle 50. The elastic member 54 can be stretched and once released will return to its original shape. The elastic member 54 is coupled to the waist belt 12 by having one end 56 inserted through a second slot 58 of the buckle 50 and then releasably attached to the buckle 50. In one embodiment, the buckle 50 includes one or more pointed male members 60 integrally attached to a rotatable axle 62. The end 56 is inserted through a slot 58 of the buckle 50 and the male members 60 are pressed through the elastic member 54 so that the elastic member 54 is attached to the buckle 50.

As an alternative, the attachment mechanism for coupling the waist belt 12 to the elastic member 54 can include a ring coupled to the waist belt 12 and a hook and loop portion coupled to the first end of the elastic member 54, wherein the hook and loop portion is configured to be inserted through the ring of the waist belt 12 and double backed to be attached to itself.

In yet another alternative, the attachment mechanism for coupling the waist belt 12 to the elastic member 54 can include a standard belt buckle that has one end attached to the waist belt 12. The elastic member 54 includes one or more holes at one end thereof. The end with the hole(s) is inserted into the buckle in a well known manner and a male member/mating section is inserted into one of the holes so that secure engagement is achieved with the male member and a desired tension can be achieved.

As shown in FIG. 1, the second end 65 of the elastic member 54 is coupled to a lower leg support 84 via an attachment mechanism, such as buckle 66. For example, the elastic member 54 extends on the posterior section of the leg and is inserted through a slot 64 of the buckle 66 that is similar in structure to buckle 50. Attachment of the elastic member 54 and the buckle 66 is accomplished in a manner similar to the attachment achieved via buckle 50.

The buckle 66 has a second slot 68 that receives a strip of material 70 therethrough. The strip of material 70 defines a V-shape. Two lower leg straps 72, 74 are attached to the strip of material 70 by inserting the ends of the straps 72, 74 into the opening defined by the V-shaped material 70. The ends of the straps 72, 74 and the material 70 are then attached to one another by a rivet or via stitching. Note that the straps 72, 74 can be two separate pieces or integral with one another.

Note that as an alternative, the buckles 50 and 66 can each be replaced with a metal ring. Furthermore, the ends of the elastic member 54 are altered to have a hook and loop system and are passed through the metal rings and looped back to engage hook and loop systems on the elastic member 54.

As shown in FIG. 1, the other ends of the straps 72, 74 are attached to a detachable knee band 76 via a rivet or stitching. The straps 72, 74 extend from a common point just behind and at least six inches superior to the knee joint to a common point on the anterior of the leg that is located below the patella where they are attached to one another above the fibial tubercle The knee band 76 is configured to encircle the user's leg in a vicinity of a patellar tendon of the user. The band 76 is made of a durable material, such as Dacron or leather, which does not stretch like the waist band, and has a length to circumvent the lower leg of the user. The band 76 has a metal loop 78 attached thereto. An end 80 of the band 76 has a hook and loop system 82 attached thereto. The hook and loop system 82 is passed through the metal loop 78 and is looped back to engage itself.

The straps 72, 74 and the knee band 76 define a lower leg support 84 that secures the elastic member 54 to a user's knee. Prior to the attachment of the lower ends of the straps 72, 74 to one another, the straps 72, 74 define an inverted V-shaped prong. Once the lower ends of the straps 72, 74 are attached to one another at the front of the band 76, the straps 72, 74 act to couple the knee band 76 to the elastic member 54. Note that band 76 may be coupled to the V-shaped prong to form an enclosed section, or may be one uniform piece that encircles the leg.

Operation of the orthosis 10 will now be described. As shown in FIG. 1, the waist belt 12 is placed around the user 16. The free ends 18, 20 of the waist belt 12 are attached to one another so that the belt 12 fits snugly on the waist of the user 16. Next, each of the bands 76 is placed around a corresponding lower leg portion located above the ankle and at the lower portion of the calf of the corresponding leg so that the material 70 is located at the back of the knee. The hook and loop system 82 is attached to itself so a snug fit is achieved. Once the waist belt 12 and the bands 76 are attached to the user, the tension of the elastic member 54 is adjusted when the leg is in a straightened conditioned by adjusting where one or more ends of the elastic member 54 are attached with their corresponding buckle. The ideal tension is achieved by having the patient stand and having the knees and hips of the patient fully extended so that the tension in the elastic members 54 is adjusted to a maximum value at this position.

Once the tension of the elastic member 54 has been adjusted, the orthosis 10 aids the user in moving in a normal manner. For example, in the standing position, the tension of the elastic member 54 causes the knee and the hip joint to extend in such a manner that the orthosis 10 mimics the actions of the gluteus maximus and the quadriceps such that the elastic member 54 creates an adjustable tensile resistance when the user moves from a sitting position. During movement of the leg from the sitting position to a standing position, the upward pull of the elastic member 54 acts on the knee in a manner similar to how the quadriceps of the leg extend and lock the knee. Furthermore, the downward pull of the elastic member 54 acting on the hips is similar to the action of the gluteus maximus when extending and locking the hips. The downward pull also causes the top of the back support 32 to be moved toward the back of the patient while the bottom portion of the back support pivots away from the back at rivet 34. Thus, the elastic member 54 and the back support 32 aid in locking the knee in an unbent state and the hip in an extended state so that the patient can walk in a lock-kneed and extended hip manner while reducing the possibility that the patient will collapse during such walking. Thus the orthosis aids in preventing the knee from bending and the patient from collapsing when performing standing and walking motions. The orthosis 10 also avoids the use of expensive, heavy and bulky metal braces that have been used in the past to straighten the legs for walking.

Note that the tension applied by the elastic member 54 can be adjusted by adjusting where the elastic member 54 is engaged to the buckles 50 and 66. Furthermore, the knee band 76 is only coupled to the elastic member 54 when the rehabilitation apparatus 10 is worn and used by the user.

Several variations of the hip knee extension assist orthosis 10 of FIG. 1 are possible. For example, the back support 32 can be lowered so that it is approximately symmetrical with respect to the waist belt 12. In other words, the back support 32 approximately extends above the waist belt 12 and below the waist belt 12 equally. Attachment to the waist belt 12 is accomplished by rivets 34 or other appropriate attachment devices.

In another variation, each strap 40 is reoriented so that it extends along the rear side of the back support 32, not the front side as shown in FIG. 1. In this variation, a bottom end 46 of strap 40 is passed over the top portion of the waist belt 12 and then passed through a slot or guide formed in the waist belt 12 below the rivet 34. Thus, the strap 40 overlaps the rivet 34 prior to being inserted into the guide or slot. The bottom end 46 of the strap 40 is then passed between the waist belt 12 and the back support 32 until it passes the bottom portion of the waist belt 12. The bottom end 46 of the strap 40 extends below the lower edge of the back support 12. The top end of the strap 40 is, passed along the rear side of the back support 32, passed over the top edge of the back support and positioned against the front side of the back support 32. The top end is attached to the back support 32 via a rivet 44. In one embodiment, the bottom end 46 of the strap 40 is passed, as with the embodiment of FIG. 1, through a slot 48 of buckle 50 which is attached at an end of elastic member 54. In this embodiment, back support 32 lacks slots 36 and 38 of the embodiment of FIG. 1.

In another variation, each strap 40 is again reoriented so that it extends along the rear side of the back support 32. In this variation, a bottom end 46 of strap 40 is passed over the entire back sides of the waist belt 12 and the back support 32 so that the bottom end 46 of the strap 40 extends below the lower edge of the back support 12. The top end of the strap 40 is passed along the rear side of the back support 32, passed over the top edge of the back support and positioned against the front side of the back support 32. The top end is attached to the back support 32 via a rivet 44. The bottom end 46 of the strap 40 is passed through a metal loop attached to an end of a hard plastic tongue element that is overlapped by the strap 40. The bottom end 46 includes a buckle 50 attached thereto. The elastic member 54 engages the buckle 50 in a manner similarly described with respect to the embodiment of FIG. 1.

The tongue element may be rectangular in shape and has a top end that overlaps a midsection of a rear portion of the waist belt 12. The top end of the tongue element is overlapped by the strap 40. Furthermore, the top end of the tongue element, the waist belt 12, the strap 40 and the back support 32 are attached to one another by a rivet 34. The above described variations of the strap 40 can be used with the back support 32 of FIG. 1 or the symmetrical back support described previously. In the case of being used with the symmetric-like back support, the tension in the strap 40 will cause a force to be applied to the top portion of the symmetric-like back support in a direction away from the back of the user. The symmetric nature of the back support causes the back support to pivot about a line situated approximately midway on the waist belt 12 and extending along the length of the waist belt 12. Thus, lower part of the back support will rotate forward toward the back of the user and engage the lower lumbar areas of the body, such as the sacrocoxyl area or the buttocks.

Once the tension of the elastic member 54 has been adjusted, the orthosis aids the user in moving in a normal manner. For example, in the standing position, the tension of the elastic member 54 causes the knee and the hip joint to extend in such a manner that the orthosis mimics the actions of the gluteus maximus and the quadriceps such that the elastic member 54 creates an adjustable tensile resistance when the user moves from a sitting position During movement of the leg from the sitting position to a standing position, the upward pull of the elastic member 54 acts on the knee in a manner similar how the quadriceps of the leg extend and lock the knee. Furthermore, the downward pull of the elastic member 54 acting on the hips is similar to the action of the gluteus maximus when extending and locking the hips. In particular, the elastic member 54 pulls downward on the back support 32 in such a manner so that the lower portion of the back support 32 rotates towards or into the sacral area of the lower back of the patient thereby causing posterior pelvic tilt and extending the hip joint. Thus, the elastic member 54 and the back support 32 aid in locking the knee in an unbent state and the hip in an extended state so that the patient can walk in a lock-kneed and extended hip manner while reducing the possibility that the patient will collapse during such walking. Thus the orthosis aids in preventing the knee from bending and the patient from collapsing when performing standing and walking motions.

In order to aid the pivoting about the line mentioned above, the waist belt 12 can be altered so that a convex pad is inserted in the central portion of the belt that lies over the symmetric-like back support. The apex of the pad lies nearest to the user. In this embodiment, the rear face of the pad has one or more connection elements, such as the hook and loop system known by the trademark Velcro. The connection elements of the pad engage engagement elements attached to the front surface of the back support 32. Alternatively, the pad can be connected to the back support 32 via rivets 34. The pad is preferably made of polyethylene or other moderately firm foam-like materials.

In another variation, the slots 36, 38 of the symmetric-like back support mentioned previously are removed. Furthermore, the cylinders 52 and their associated metal flange are removed. In their place, a two single loops of material or metal loops are attached to the rear of the waist belt 12 via the rivets 34 shown in FIG. 1. In this case, the straps 40 are passed through the loops and then are engaged with buckles 50 in the manner described previously. In operation, the loops allow the elastic members 54 to move to the side of the leg when the user is sitting. This is in contrast with the FIG. 1 variation wherein the elastic members would remain at the rear of the leg when the user is sitting. Having the elastic members 54 at the side of the leg while sitting generates less tension on the leg than when the elastic members 54 are at the rear of the leg. In a variation of this, the loops can be removed resulting in the elastic members 54 moving further to the side of the leg during sitting and thus reducing tension further.

Figure 2:
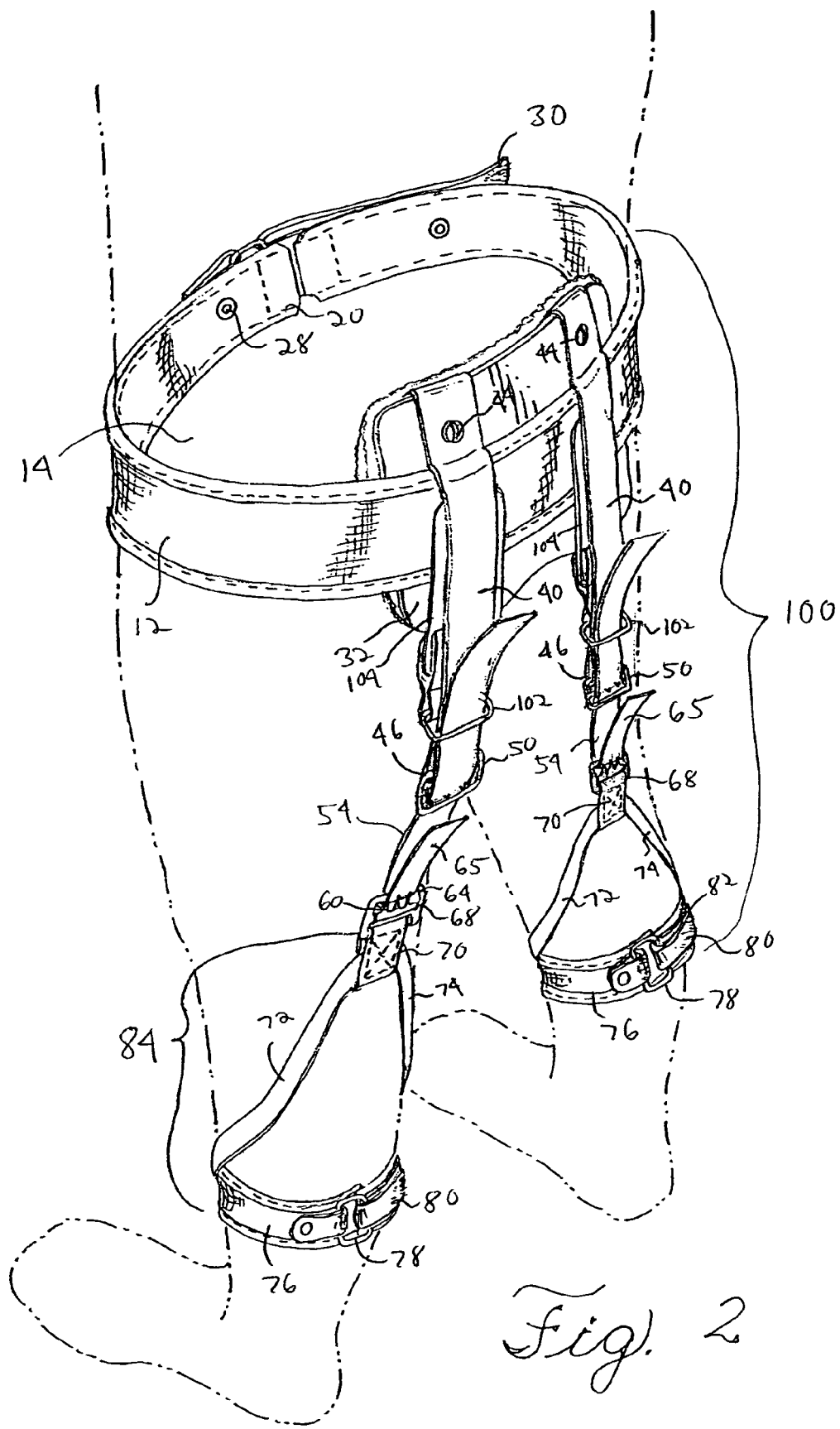
FIG. 2 is a rear, perspective view of a second embodiment of a muscle imitation apparatus in accordance with the present invention.

An alternative embodiment of a muscle imitation or ambulation apparatus, such as a hip flexion orthosis 100, is shown in FIGS. 2 and 3, wherein like numerals represent like elements as described previously with respect to the FIG. 1 embodiment. In this variation, a bottom end 46 of strap 40 is passed over the entire back sides of the waist belt 12 and the back support 32 (symmetrically positioned relative to the waist belt 12) so that the bottom end 46 of the strap 40 extends below the lower edge of the back support 12. The top end of the strap 40 is, passed along the rear side of the back support 32, passed over the top edge of the back support and positioned against the front side of the back support 32. The top end is attached to the back support 32 via a rivet 44. The bottom end 46 of the strap 40 is passed through a metal loop 102 attached to an end of a hard plastic tongue element 104 that is overlapped by the strap 40. The bottom end 46 includes a buckle 50 attached thereto. The elastic member 54 engages the buckle 50 in a manner similarly described with respect to the embodiment of FIG. 1.

The tongue element 104 may be rectangular in shape and has a top end 106 that overlaps a midsection of a rear portion of the waist belt 12. The top end 106 of the tongue element 104 is overlapped by the strap 40. Furthermore, the top end 106 of the tongue element 104, the waist belt 12 and the back support 32 are attached to one another by a rivet 34.

In operation, each tongue element 104 extends along the back of its corresponding leg when the user is in an upright position as shown in FIG. 2. When the user sits down, the tongue elements 104 may release tension in their elastic members 54 by pivoting away from each other about rivets 34. Besides relieving tension, such movement by the tongue elements 104 provides more comfort to the user since the user does not sit directly on the tongue elements 105 and the elastic member 54. Note that the user may manually pivot the tongue elements 104 away from each other about rivets 34 prior to sitting down. When the user rises from the sitting position to a standing position, the tongue elements 104 and the elastic members 54 return to their aligned positions along the back of the legs as shown in FIG. 2.

As shown in FIG. 2, the bottom end of each elastic member 54 is attached to a corresponding previously described lower leg support 84 via buckle 66 in the same manner as described previously with respect to the embodiment of FIG. 1.

The tension in the strap 40 of FIG. 2 will cause a force to be applied to the top portion of the symmetric-like back support in a direction away from the back of the user. The symmetric nature of the back support causes the back support to pivot about a line situated approximately midway on the waist belt 12 and extending along the length of the waist belt 12. Thus, lower part of the back support will rotate forward toward the back of the user and engage the lower lumbar areas of the body, such as the sacrocoxyl area or the buttocks.

In order to aid the pivoting about the line mentioned above, a convex pad 108 is attached to a front surface of the back support 132, wherein the apex 110 of the pad 108 lies nearest to the user. As shown in FIG. 4, the convex pad 108 has a trapezoidal-like cross-section. In this embodiment, the rear face of the pad has one or more connection elements, such as hook and loop systems 112 known by the trademark Velcro. The connection elements of the pad 108 engage engagement elements (not shown) attached to the front surface of the back support 32. Alternatively, the pad can be connected to the back support 32 via rivets 34. The pad is preferably made of polyethylene or other moderately firm foam-like materials.

Once the tension of the elastic member 54 has been adjusted, the orthosis 100 aids the user in moving in a normal manner as described previously with respect to the embodiment of FIG. 1.

An alternative embodiment of a muscle imitation or ambulation apparatus, such as a hip flexion orthosis will be described in which elements similar to those described previously with respect to FIGS. 1-4 will use similar numerals. For example, the alternative embodiment may include the elastic members 54 and the lower leg supports 84 being attached to the front of waist belt 12 instead of the rear as shown in FIG. 1. Accordingly, this embodiment shall be called a frontal flexion orthosis. In this embodiment, first ends of elastic members 54 are attached to the waist belt 12 directly via rivets. The other ends of the elastic members 54 extend along the anterior sections of the leg and are attached to corresponding lower leg supports via buckles 66 in the manner described previously. Note that the lower leg support 84 of orthoses 10 and 100 has a different structure than the lower leg support of the above mentioned front flexion orthosis. In particular, upper ends of the straps 72, 74 of the lower leg support of the front flexion orthosis are attached at a common point above the patella at the anterior portion of the leg. In contrast with lower leg support 84 of FIGS. 1-4, the lower ends of the straps 72, 74 of the lower leg support of the front flexion orthosis are not attached to one another at a common point of the band 76. Instead, the lower ends of the straps 72, 74 are attached to band 76 at the sides of the leg so that the lower ends are separated from one another at opposing sides of the leg. Thus, the straps 72, 74 define of the front flexion orthosis an inverted V-shaped prong as viewed when looking at the front of the user. Accordingly, each knee band 76 is only coupled to the elastic member 54 when the rehabilitation apparatus 100 is worn and used by the user. Again, the tension in the elastic members 54 can be adjusted by adjusting where the elastic members 54 are attached to the buckle 66. In this embodiment, plastic rollers 52 along with corresponding metal loops and flanges, as described previous with respect to FIG. 1, can be attached to the front of the waist belt 12. The front flexion orthosis may not employ a back support 32.

One difference between the orthoses 10 and 100 of FIGS. 1-4 and the above mentioned frontal flexion orthosis is that the elastic members 54 of the frontal flexion orthosis extend along the front or anterior portion of the leg while the elastic members 54 of orthoses 10 and 100 extend along the back or posterior portion of the leg.

Operation of the rehabilitation apparatus of the frontal flexion orthosis will now be described. In particular, the waist belt 12 is placed around and attached to the user 16 in the same manner as described with respect to the embodiments of FIGS. 1-4 so as to snugly fit the waist of the user 16. Next, each of the bands 76 is placed around a corresponding lower leg portion located above the ankle and at the lower portion of the calf of the corresponding leg so that the material 70 is located just above the knee. The hook and loop system 82 of the bands are attached to themselves so a snug fit is achieved. Once the waist belt 12 and the bands 76 are attached to the user, the tension of the elastic member 54 when the leg is in a straightened conditioned is adjusted by adjusting where one or more ends of the elastic member 54 are attached with their corresponding buckle. The ideal tension is achieved when the correct tension offsets the weight of the leg and therefore allows the muscle needed to lift the leg to function when initiating a forward step.

Once the tension of the elastic members 54 have been adjusted, the user moves in a normal manner in order to mimic the muscle action of the user by augmenting weak hip flexor muscles. For example, in the standing position, the tension of the elastic member is countered by the hip extensor muscles. During forward movement of the leg, the upward and forward motion of the leg is assisted by the tension of the elastic member 54, thus making it easier to advance the leg and facilitates clearance of the foot past the floor and thereby causes the patient's gait to be more natural and to conserve energy and stamina of the patient.

Note that while the embodiment of the frontal flexion orthosis shows the use of an elastic member 54 with each leg, it is contemplated that most human conditions that would benefit from orthosis 54 are asymmetrical in nature, i.e., conditions where the muscles are weakened asymmetrically about the body. For example, conditions such as stroke and polio can lead to the muscles of one side of the patient to be weaker than those of another side. For such conditions, it is possible to remove one of the elastic members 54 of the frontal flexion orthosis so that the remaining elastic member 54 is used with the weaker leg of the patient. The elastic member 54 of the frontal flexion orthosis can be used to aid in maintaining mobility in conditions like polio and can be used to aid in strengthening the muscles in conditions like a stroke. In the case of the orthoses 10 and 100 mentioned previously, muscular dystrophy is a symmetric condition and so two elastic members 54 are used. Of course, if an asymmetric situation results, one of the elastic members 54 can be removed for the orthoses 10 and 100.

With the above descriptions in mind, rehabilitation of a person via physical therapy is accomplished by first identifying a compromised body member of a patient, such as leg or hip muscles, or a physical condition of a patient, such as muscle weakness caused by muscular dystrophy, stroke or polio or a number of conditions that result in hip flexor weakness, that requires physical therapy. Based on the identification, either the apparati 10 or 100 or the frontal flexion orthosis are worn in the manner described previously. The tension of elastic members 54 are adjusted to provide a desired therapy for the muscles to be rehabilitated. The user then wears and uses the device in the manner described previously for a specific time or indefinitely in order to provide sufficient therapy to improve the condition of the muscles to be rehabilitated or to improve the function and mobility of muscles whose condition cannot be reversed such as muscular dystrophy.

The foregoing description is provided to illustrate the invention, and is not to be construed as a limitation. Numerous additions, substitutions and other changes can be made to the invention without departing from its scope as set forth in the appended claims. For example, in each of the embodiments of FIGS. 1-4 only one elastic member and lower leg support is used for a particular leg that needs rehabilitation.

I claim:

1. A muscle imitation apparatus comprising:
   a waist belt configured to be secured around a user's waist;
   an elastic member having a first end and a second end, wherein said first end is coupled to said waist belt;
   a lower leg system coupled to said second end of said elastic member, wherein said lower leg system is configured to encircle said user's leg in a vicinity of a patellar tendon of said user, such that said elastic member creates an adjustable tensile resistance when said user moves said leg and said lower leg system is only coupled to said elastic member when said muscle imitation apparatus is worn by said user; and
   a back support attached to said waist belt, wherein said first end of said elastic member is coupled to said back support and said back support is made of a durable plastic material, wherein a lower portion of said back support has a slot through which said first end of said elastic member passes through and said first end extends over a top of said back support and is attached to a rear side of said back support by a rivet.

2. The muscle imitation apparatus of claim 1, wherein said lower leg system comprises:

a band to be attached to a portion of said user's leg below a patella of said user's leg; and
a first strap comprising:
  a first end attached to said second end of said elastic member; and
  a second end attached to a portion of said band located at an anterior portion of said user's leg; and
a second strap comprising:
  a first end attached to said second end of said elastic member; and
  a second end attached to said portion of said band located at an anterior portion of said user's leg.

3. The muscle imitation apparatus of claim 1, further comprising an attachment mechanism for coupling said first end of said elastic member to said waist belt.

4. The muscle imitation apparatus of claim 3; wherein said attachment mechanism comprises:
  a ring coupled to said waist belt; and
  a hook and loop portion coupled to said first end of said elastic member, wherein said hook and loop portion is configured to be inserted through said ring of said waist belt to couple said elastic member to said waist belt.

5. The muscle imitation apparatus of claim 3 wherein said attachment mechanism comprises:
  a buckle comprising a mating section, wherein said buckle is coupled to said waist belt; and
  a hole disposed in said first end of said elastic member, wherein said hole is configured to securely engage said mating section of said buckle.

6. The muscle imitation apparatus of claim 1, wherein said elastic member is disposed along an anterior section of said user's leg.

7. The muscle imitation apparatus of claim 1, wherein said back support is asymmetrically positioned with respect to said waist belt.

8. The muscle imitation apparatus of claim 1, wherein as viewed from a front of a user of said muscle imitation apparatus said back support has a generally flat portion that overlaps said waist belt and is concave-like for those portions of said back support that are above said waist belt.

9. A muscle imitation apparatus comprising:
  a waist belt configured to be secured around a user's waist;
  an elastic member having a first end and a second end, wherein said first end is coupled to said waist belt;
  a lower leg system coupled to said second end of said elastic member, wherein said lower leg system is configured to encircle said user's leg in a vicinity of a patellar tendon of said user, such that said elastic member creates an adjustable tensile resistance when said user moves said leg and said lower leg system is only coupled to said elastic member when said muscle imitation apparatus is worn by said user; and
  a back support attached to said waist belt, wherein said first end of said elastic member is coupled to said back support and said back support is made of a durable plastic material, wherein a lower portion of said back support has a slot through which said first end of said elastic member passes through and said first end extends over a top of said back support and is attached to a front side of said back support by a rivet.

10. An apparatus suitable for imitating one or muscles of a user during physical therapy, the apparatus comprising:
  an adjustable waist belt configured to be secured around a user's waist;
  an elastic member having a first end and a second end;
  means for coupling said first end of said elastic member to said waist belt;
  means for securing said second end of said elastic member to said user's knee;
  means for tensioning said elastic member between said waist belt and said means for securing; and
  a back support attached to said waist belt, wherein said first end of said elastic member is coupled to said back support and said back support is made of a durable plastic material, wherein a lower portion of said back support has a slot through which said first end of said elastic member passes through and said first end extends over a top of said back support and is attached to a rear side of said back support by a rivet.

11. The apparatus of claim 10, wherein said elastic member is disposed along an anterior section of said user's leg.

12. The apparatus of claim 10, wherein said back support is asymmetrically positioned with respect to said waist belt.

13. The apparatus of claim 10, wherein as viewed from a front of a user of said muscle imitation apparatus said back support has a generally flat portion that overlaps said waist belt and is concave-like for those portions of said back support that are above said waist belt.

14. An apparatus suitable for imitating one or muscles of a user during physical therapy, the apparatus comprising:
  an adjustable waist belt configured to be secured around a user's waist;
  an elastic member having a first end and a second end;
  means for coupling said first end of said elastic member to said waist belt;
  means for securing said second end of said elastic member to said user's knee;
  means for tensioning said elastic member between said waist belt and said means for securing; and
  a back support attached to said waist belt, wherein said first end of said elastic member is coupled to said back support and said back support is made of a durable plastic material, wherein a lower portion of said back support has a slot through which said first end of said elastic member passes through and said first end extends over a top of said back support and is attached to a front side of said back support by a rivet.

15. An apparatus suitable for imitating one or more muscles of a human user during physical therapy, wherein said apparatus is configured to be used in conjunction with the human user having a waist and a leg comprising a knee, said apparatus comprising:
  an adjustable waist belt configured to be secured around said human user's waist;
  a lower leg support configured to encircle said human user's leg in the vicinity of said knee;
  an elastic member configured to provide an adjustable tensile resistance between said waist belt and said knee band; and
  a back support attached to said waist belt and said elastic member and said back support is made of a durable plastic material, wherein a lower portion of said back support has a slot through which said first end of said elastic member passes through and said first end extends over a top of said back support and is attached to a rear side of said back support by a rivet.

16. The apparatus of claim 15, wherein said elastic member is disposed along an anterior section of said human user's leg.

17. The apparatus of claim 15, wherein said back support is asymmetrically positioned with respect to said waist belt.

18. The apparatus of claim 15, wherein as viewed from a front of a user of said muscle imitation apparatus said back support has a generally flat portion that overlaps said waist belt and is concave-like for those portions of said back support that are above said waist belt.

19. An apparatus suitable for imitating one or more muscles of a human user during physical therapy, wherein said apparatus is configured to be used in conjunction with the human user having a waist and a leg comprising a knee, said apparatus comprising:

an adjustable waist belt configured to be secured around said human user's waist;

a lower leg support configured to encircle said human user's leg in the vicinity of said knee;

an elastic member configured to provide an adjustable tensile resistance between said waist belt and said knee band; and a back support attached to said waist belt and said elastic member and said back support is made of a durable plastic material, wherein a lower portion of said back support has a slot through which said first end of said elastic member passes through and said first end extends over a top of said back support and is attached to a front side of said back support by a rivet.

* * * * *